(12) United States Patent
Helentjaris et al.

(10) Patent No.: US 7,074,985 B2
(45) Date of Patent: Jul. 11, 2006

(54) DEVELOPMENT OF A STRESS-RESPONSIVE PROMOTER FROM MAIZE

(75) Inventors: Timothy G. Helentjaris, Ankeny, IA (US); Hank W. Bass, Tallahassee, FL (US); Rebecca S. Boston, Raleigh, NC (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 87 days.

(21) Appl. No.: 10/365,049

(22) Filed: Feb. 12, 2003

(65) Prior Publication Data

US 2003/0217393 A1    Nov. 20, 2003

Related U.S. Application Data

(60) Provisional application No. 60/357,376, filed on Feb. 15, 2002.

(51) Int. Cl.
*C12N 15/09* (2006.01)
*C12N 15/82* (2006.01)
*A01H 5/00* (2006.01)

(52) U.S. Cl. ............. 800/278; 800/298; 800/295; 800/320; 800/317; 435/320.1; 435/468

(58) Field of Classification Search ............. 800/278, 800/320.1, 317.1, 320.2, 320.3, 287, 298, 800/295; 435/320.1, 467, 69.1, 468; 536/23.4
See application file for complete search history.

(56) References Cited

U.S. PATENT DOCUMENTS 5,332,808 A    7/1994    Boston et al.
5,552,140 A    9/1996    Boston et al.

OTHER PUBLICATIONS

Kim et al. Plant Molecular Biology, vol. 24, pp. 105-117, 1994.*
Benfey et al. Science 1990, vol. 250, pp. 959-966.*
Keller et al. The Plant Cell, vol. 3, pp. 1051-1061, 1991.*
Bass, et al., "Cloning and Sequencing of a Second Ribosome-Inactivating Protein Gene from Maize (Zea mays L.)", Plant Physiol. (1995) 107:661-662.
Bass, et al., "A MaizeRibosome-Inactivating Protein Is Controlled by the Transcriptional Activator Opaque-2", The Plant Cell, 4:225-234 (1992).
Nielsen, et al., "Ribosome-Inactivating Proteins: A Plant Perspective", Annu. Rev. Plant Physiol. Plant Mol. Biol. 52:785-816 (2001).

* cited by examiner

*Primary Examiner*—Medina A. Ibrahim
(74) *Attorney, Agent, or Firm*—Pioneer Hi-Bred International, Inc.

(57) ABSTRACT

The present invention provides a composition and method for regulating expression of heterologous nucleotide sequences in a plant. The method comprises transforming a plant cell to contain a heterologous nucleotide sequence operably linked to the stress-responsive promoter of the present invention and regenerating a stably transformed plant from the transformed plant cell.

16 Claims, No Drawings

SEQUENCE LISTING

<160> NUMBER OF SEQ ID NOS: 4

<210> SEQ ID NO 1
<211> LENGTH: 1824
<212> TYPE: DNA
<213> ORGANISM: Zea mays

<400> SEQUENCE: 1

| | | | | | | |
|---|---|---|---|---|---|---|
| taatcattac | ttaggtttta | ttttaccaca | tttttatttt | gttttcccct | gttccttttc | 60 |
| tcttcatttc | cattcaatta | atgggatgtt | tgataccttc | gattgcacc | aacctgttca | 120 |
| attgtacttc | agatatcatc | ttctttgatt | gtctctcacc | tctgctttgc | ttcagtacct | 180 |
| gtattttttc | ccatgaccct | gaattctatt | tgcccacatc | acaacacttg | cttcttctcg | 240 |
| aacaaataaa | taaacaaact | tcacagaacc | gtagttttta | tttctatcca | tacattgtca | 300 |
| gtttgatgat | ccagacgagg | tagatgaaga | gaaagaagtt | gagtatgaag | aaatcgagga | 360 |
| ggaggttgag | tatgaagaga | tagaggagga | ttaagaaatt | gatggtgtgt | gtgaatttga | 420 |
| tgctaatgat | gaaagtaaaa | tggtcgatgt | tgatgcgaat | gatgagaatg | aaaaacggaa | 480 |
| gcatgctgag | cttcttgctc | ttactcatgg | agctgaagtt | tatgttgggg | catatcttct | 540 |
| aatgtatctt | ctgaaaatct | caaacaacta | ttctgaagat | ctcaaacaac | tatttgaatc | 600 |
| tgttgggagc | tgaagtttat | gttgggcata | tcttctgatg | tatcttctct | actttagctt | 660 |
| ttgcatttct | attctctgca | aatttagagt | ccctttttct | gcaggttgta | tatccttatt | 720 |
| gtgtcgcatg | ttttggccga | tgctacccga | attgggcaac | aatgatctca | gaatgtcatg | 780 |
| acacacattt | gacattgtcc | atctactatt | gatcgtgcct | gcaagattga | acagatcaag | 840 |
| ctttgaaaga | aggatgtcaa | aaggcattgg | tgattgaaca | aaggcagtca | agagccattg | 900 |
| aaagaaagtt | gtatgttgag | agcactaaga | caacggtctt | acagtgtaca | aaatatatca | 960 |
| ctgaatagtt | atatcttact | tttttagcac | ttgagcaatt | aaactttag | ttgttcattg | 1020 |
| ttatagtcga | tacccagata | tcatacagtg | tctaatatga | acatttaatt | ttcatgtaat | 1080 |
| cattatgctc | taacattttt | taaaaaataa | tgtgctgttg | caacgcacgg | gcatcgtact | 1140 |
| agtaaagtat | atatatatat | atatatatat | agacttttac | cattcaaaaa | aatttgaggg | 1200 |
| cctcaatttt | ttgtttcgcc | ccgggtccat | gaaacctagg | gaccggccgt | gtatatatat | 1260 |
| ggtcttccct | tcactaacta | tatagagaca | gatcacatcg | gaataaaaga | aatttataga | 1320 |
| ccaaatcgga | aacctaaaaa | ccaaaaaccg | agcaattcgg | tctattcggt | tttagttagc | 1380 |
| aggttcaaaa | tgtccggtcc | tactaatact | caacaatgat | taagaaccga | tctgccatat | 1440 |
| tttaaaaaat | tatggaccgg | aataacacat | agtgaaaagt | ttaaggagcg | aaaatatttt | 1500 |
| tttttccttg | gcaatttgga | cggcacgcgg | agactggcag | accgcatcct | cgtgaagcac | 1560 |
| gttgtccatg | cctgaagaga | gtattctgta | ttcgcagtat | tcctgcattt | aaagtttgg | 1620 |
| tgagcgaatc | aataattggc | ataaataatg | ctaccgacgc | atcaccacat | agtacgtacc | 1680 |
| atagtcatcc | ttatcctatc | gaattaccta | catgcccaac | cctcccacta | catatatctg | 1740 |
| caacgagcgc | atcgccaatt | cacaatgcca | attgccagca | acccatccat | actttcagct | 1800 |
| gttgatacaa | aaagagaaga | gaga | | | | 1824 |

<210> SEQ ID NO 2
<211> LENGTH: 1107
<212> TYPE: DNA
<213> ORGANISM: Zea mays

-continued

```
<400> SEQUENCE: 2
gaattcgccc ttgttttggc cgatgctacc cgaattgggc aacaatgatc tcagaatgtc      60
atgacacaca tttgacattg tccatctact attgatcgtg cctgcaagat tgaacagatc     120
aagctttgaa agaaggatgt caaaaggcat tggtgattga acaaaggcag tcaagagcca     180
ttgaaagaaa gttgtatgtt gagagcacta agacaacggt cttacagtgt acaaaatata     240
tcactgaata gttatatctt acttttttag cacttgagca attaaacttt tagttgttca     300
ttgttatagt cgatacccag atatcataca gtgtctaata tgaacattta attttcatgt     360
aatcattatg ctctaacatt ttttaaaaaa taatgtgctg ttgcaacgca cgggcatcgt     420
actagtaaag tatatatata tatatatata tatagacttt taccattcaa aaaaatttga     480
gggcctcaat tttttgtttc gccccgggtc catgaaacct agggaccggc cgtgtatata     540
tatggtcttc ccttcactaa ctatatagag acagatcaca tcggaataaa agaaatttat     600
agaccaaatc ggaacctaa aaaccaaaaa ccgagcaatt cggtctattc ggttttagtt     660
agcaggttca aaatgtccgg tcctactaat actcaacaat gattaagaac cgatctgcca     720
tattttaaaa aattatggac cggaataaca catagtgaaa agtttaagga gcgaaaatat     780 tttttttttcc ttggcaattt ggacggcacg cggagactgg cagaccgcat cctcgtgaag     840
cacgttgtcc atgcctgaag agagtattct gtattcgcag tattcctgca tttaaaagtt     900
tggtgagcga atcaataatt ggcataaata atgctaccga cgcatcacca catagtacgt     960
accatagtca tccttatcct atcgaattac ctacatgccc aaccctccca ctacatatat    1020
ctgcaacgag cgcatcgcca attcacaatg ccaattgcca gcaacccatc catactttca    1080
gctgttgata caaaaagaga agagacc                                        1107

<210> SEQ ID NO 3
<211> LENGTH: 25
<212> TYPE: DNA
<213> ORGANISM: Zea mays

<400> SEQUENCE: 3
gttttggccg atgctacccg aattg                                            25

<210> SEQ ID NO 4
<211> LENGTH: 29
<212> TYPE: DNA
<213> ORGANISM: Zea mays

<400> SEQUENCE: 4
tgatgcgtcg gtaccatggt tatgccaat                                        29
```

DEVELOPMENT OF A STRESS-RESPONSIVE PROMOTER FROM MAIZE

CROSS REFERENCE TO RELATED APPLICATIONS

This application claims the benefit of, and hereby incorporates by reference, provisional patent application 60/357,376, filed Feb. 15, 2002.

FIELD OF THE INVENTION

The present invention relates to the field of plant molecular biology, more particularly to regulation of gene expression in plants.

BACKGROUND OF THE INVENTION

Throughout their lives, plants are routinely subjected to a variety of stresses which act to impede or alter growth and development processes. Because it negatively impacts plant growth and development processes, stress to agricultural plants has a negative economic impact in the form of reduced yields, increased expenditures to ameliorate the effects of stress, or both. Given the world's increasing human population and the diminishing land area available for agriculture, improving agricultural productivity is of paramount importance. Thus, there is a need for crop plants that are better able to tolerate stresses and maintain productivity under unfavorable conditions.

While traditional plant breeding approaches will continue to be important for improving agricultural plants, the new strategies that are likely to have the most significant impact on crop improvement will involve genetic engineering. A thorough understanding of the molecular and cellular mechanisms used by plants to avoid or tolerate stresses may help in the development of new strategies to improve the stress tolerance of agricultural plants.

Stresses to plants may be caused by both biotic and abiotic agents. For example, biotic causes of stress include infection with a pathogen, insect feeding, parasitism by another plant such as mistletoe, and grazing by animals. Abiotic stresses include, for example, excessive or insufficient available water, excessive or insufficient light intensity, temperature extremes, synthetic chemicals such as herbicides, and excessive wind. Yet plants survive and often flourish, even under unfavorable conditions, using a variety of internal and external mechanisms for avoiding or tolerating stress. Plants' physiological responses to stress reflect changes in gene expression.

While manipulation of stress-induced genes may play an important role in improving plant tolerance to stresses, it has been shown that constitutive expression of stress-inducible genes has a severe negative impact on plant growth and development when the stress is not present. (Kasuga et al., Nature Biotechnology 17:287–291) Therefore, there is a need in the art for methods employing regulatory elements responsive to stress, to provide a means to control and direct expression of genes involved in stress tolerance.

SUMMARY OF THE INVENTION

It is an object of the present invention to provide an isolated promoter capable of driving transcription in response to stress, including the stress of insufficient available water.

Therefore, in one aspect, the present invention relates to a functional stress-responsive promoter comprising the isolated nucleic acid segment set forth in SEQ ID NOS: 1 or 2, or functional fragments or variants of said sequences.

In other aspects, the present invention relates to expression cassettes comprising the promoter operably linked to a nucleotide sequence, vectors containing the expression cassette, and plants stably transformed with at least one such expression cassette.

It is another object of the present invention to provide a method of improved control of an endogenous or exogenous product in a transformed plant.

It is a further object of the present invention to provide a method for effecting useful changes in the phenotype of a transformed plant.

It is a further object of the present invention to provide a method for modulating the development of a transformed plant.

In a further aspect, the present invention relates to a method for modulating gene expression in a stably transformed plant comprising the steps of (a) transforming a plant cell with an expression cassette comprising the promoter of the present invention operably linked to at least one nucleotide sequence; (b) growing the plant cell under appropriate growing conditions and (c) regenerating a stably transformed plant from the plant cell wherein said linked nucleotide sequence is expressed under conditions of stress.

DETAILED DESCRIPTION OF THE INVENTION

In accordance with the invention, a nucleotide sequence is provided that modulates initiation of transcription in response to stress. The sequence of the invention comprises transcriptional initiation regions associated with gene expression in response to stress. Thus, the compositions of the present invention comprise a novel nucleotide sequence for a stress-induced plant promoter.

As used herein, a "recombinant expression cassette" or "expression cassette" is a nucleic acid construct, generated recombinantly or synthetically, comprising a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the expression cassette portion of an expression vector includes, among other sequences, a promoter and a nucleic acid to be transcribed.

An "expression profile" is the result of detecting a representative sample of expression products from a cell, tissue, or whole organism, or a representation (picture, graph, data table, database, etc.) thereof. For example, many RNA expression products of a cell or tissue can be simultaneously detected on a nucleic acid array, or by the technique of differential display or modification thereof such as CuraGen's GeneCalling™ technology. A "portion" or "sub-portion" of an expression profile, or a "partial profile" is a subset of the data provided by the complete profile, such as the information provided by a subset of the total number of detected expression products.

By "heterologous nucleotide sequence" is intended a sequence that is not naturally occurring with the promoter sequence. While this nucleotide sequence is heterologous to the promoter sequence, it may be endogenous (native) or exogenous (foreign) to the plant host.

As used herein, "nucleic acid" includes reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired manner, such as under conditions of water stress, can be identified, isolated, and used with other core promoters.

Expression of heterologous DNA sequences in a plant host is dependent upon the presence of an operably-linked promoter that is functional within the plant host. Choice of the promoter sequence will determine when and where within the plant the heterologous DNA sequence is expressed. Where continuous expression is desired throughout the cells of a plant, constitutive promoters are utilized. In contrast, where gene expression in response to a stimulus is desired, inducible promoters are the regulatory element of choice. Where expression in specific tissues or organs is desired, tissue-preferred promoters are used. That is, these promoters can drive expression in specific tissues or organs. Additional regulatory sequences upstream and/or downstream from the core promoter sequence can be included in expression cassettes of transformation vectors to bring about varying levels of expression of heterologous nucleotide sequences in a transgenic plant. See, for example, U.S. Pat. No. 5,850,018.

The isolated promoter sequence of the present invention can be modified to provide for a range of expression levels of the heterologous nucleotide sequence. Less than the entire promoter region can be utilized and the ability to drive seed-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence. However, shorter segments of a promoter may be effective in driving expression, and may particularly enhance expression within specific tissues.

It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The term "isolated" refers to material, such as a nucleic acid or a protein, which is substantially or essentially free from components which normally accompany or interact with it as found in its natural environment. The isolated material optionally comprises material not found with the material in its natural environment; or if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome.

Methods for isolation of promoter regions are well known in the art. One method is described in U.S. patent application Ser. No. 09/387,720 filed Aug. 30, 1999, herein incorporated by reference.

A sequence for the promoter region of the present invention, comprising 1824 nucleotides 5' to the RIP2 coding sequence, is set forth in SEQ ID NO: 1. SEQ ID NO: 2 comprises 1107 nucleotides 5' to the RIP2 coding sequence and includes additional restriction sites to facilitate manipulation of the promoter region.

U.S. Pat. Nos. 5,332,808 and 5,552,140 disclosed the RIP2 gene and 989 nucleotides 5' thereto. (See also GenBank L26305 and I25465).

The promoter region of the invention may be isolated from any plant, including, but not limited to, barley (*Hordeum vulgare*), maize (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanut (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oat (*Avena sativa*), vegetables, ornamentals, and conifers. Preferably, plants include barley, maize, soybean, sunflower, safflower, canola, wheat, rye, alfalfa, and sorghum.

Promoter sequences from other plants may be isolated according to well-known techniques based on their sequence homology to the promoter sequence set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al., eds., (1990) *PCR Protocols, A Guide to Methods and Applications*, Academic Press).

The terms "stringent conditions" or "stringent hybridization conditions" include reference to conditions under which a probe will hybridize to its target sequence, to a detectably greater degree than to other sequences (e.g., at least 2-fold over background). Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 1000 nucleotides in length to about 250 nucleotides in length.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). See also Sambrook et al. (1989) *Molecular Cloning: A Laboratory Manual* (2nd ed. Cold Spring Harbor Laboratory, Cold Spring Harbor, N.Y.).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m$=81.5° C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York).

See also Sambrook et al. (1989) *Molecular Cloning: A Laboratory Manual* (2d ed., Cold Spring Harbor Laboratory Press, Plainview, N.Y.). Thus, isolated sequences that retain the promoter function of the invention and hybridize under stringent conditions to the sequences disclosed herein, or to fragments thereof, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99% or more homologous with the disclosed sequence. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99% or more sequence identity.

Sequences isolated based on their sequence identity to the entire promoter sequence set forth herein or to fragments thereof are encompassed by the present invention.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5:

151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994).

Sequence fragments with high percent identity to the sequence of the present invention also refer to those fragments of a particular promoter nucleotide sequence disclosed herein that operate to promote the stress-induced expression of an operably-linked heterologous nucleotide sequence. These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments can be obtained by use of restriction enzymes to cleave the naturally occurring promoter nucleotide sequences disclosed herein; by synthesizing a nucleotide sequence from the naturally occurring promoter DNA sequence; or through the use of PCR technology. See particularly, Mullis et al. (1987) *Methods Enzymol.* 155:335–350, and Erlich, ed. (1989) *PCR Technology* (Stockton Press, N.Y.). Again, variants of these promoter fragments, such as those resulting from site-directed mutagenesis, are encompassed by the compositions of the present invention.

Biologically active variants of the promoter sequence are also encompassed by the composition of the present invention. A regulatory "variant" is a modified form of a regulatory sequence wherein one or more bases have been modified, removed or added. For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digestion of a clone with this enzyme produces unidirectional nested deletions.

One example of a regulatory sequence variant is a promoter formed by one or more deletions from a larger promoter. The 5' portion of a promoter up to the TATA box near the transcription start site can be deleted without abolishing promoter activity, as described by Zhu et al., *The Plant Cell* 7: 1681–89 (1995). Such variants should retain promoter activity. Biologically active variants include, for example, the native promoter sequences of the invention having one or more nucleotide substitutions, deletions or insertions. Promoter activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

The nucleotide sequence for the promoter of the invention, as well as fragments and variants thereof, can be provided in expression cassettes along with heterologous nucleotide sequences for expression in a plant of interest, more particularly in a plant subject to stress. Such an expression cassette is provided with a plurality of restriction sites for insertion of the nucleotide sequence to be under the transcriptional regulation of the promoter. These expression cassettes are useful in the genetic manipulation of any plant to achieve a desired phenotypic response.

Genes of interest expressed under direction of the promoter of the invention can be used for varying the phenotype of transformed plants. This can be achieved by increasing expression of endogenous or exogenous products in seeds. Alternatively, the results can be achieved by providing for a reduction of expression of one or more endogenous products. General categories of genes of interest for the purposes of the present invention include, for example, those genes involved in information, such as Zinc fingers, those involved in communication, such as kinases, and those involved in housekeeping, such as heat shock proteins. More specific categories of transgenes include genes encoding important traits for agronomic quality, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms. It is recognized that any gene of interest can be operably linked to the promoter of the invention and expressed in a plant.

In a more preferred embodiment, the promoter of the instant invention modulates genes encoding proteins which act as stress-protectants in plants experiencing various abiotic stresses, including cold, dehydration, salt, etc. Examples of these genes would include the CBF/DREB family of transcription factors shown to induce pathways according protection to plants from cold, salt, and dehydration stress (Jaglo-Ottosen, K. R., (1998) *Science* 280:104–106); a calcium-dependent protein kinase whose over-expression confers tolerance to all three stresses (Saijo, Y. (2000) *The Plant Journal* 23(3):319–327); and molecular chaperone binding proteins or BIPs whose over-expression confers tolerance to water stress (Alvim, F. C., (2001) *Plant Physiol.* 126: 1042–1054). Other protein-encoding sequences which might protect against stress when coupled with stress-induced promoters could include cell cycle regulators or genes controlling carbohydrate metabolism or phytohormone levels, as has been shown in tobacco and canola with tissue-preferred promoters. (Ma, Q. H., et al., (1998) *Australian Journal of Plant Physiology* 25(1): 53–59; Roeckel, P., et al., (1997) *Transgenic Research* 6(2):133–141) Agronomic traits of plants can be improved by altering expression of genes that affect the response of seed growth and development during environmental stress (Cheikh-N et al., (1994) *Plant Physiol.* 106(1):45–51) and genes controlling carbohydrate metabolism to reduce seed abortion in maize (Zinselmeier et al. (1995) *Plant Physiol.* 107(2):385–391). Expression of endogenous or exogenous nucleotides under the direction of the promoter may result in maintenance of a desirable plant phenotype under adverse environmental conditions.

Insect resistance genes may include, for example, *Bacillus thuringiensis* endotoxin genes, U.S. Pat. Nos. 5,366,892; 5,747,450; 5,737,514; 5,723,756; 5,593,881; Geiser et al. (1986) *Gene* 48:109; lectins, Van Damme et al. (1994) *Plant Mol. Biol.* 24:825; and the like.

Genes encoding disease resistance traits include detoxification genes, such as against funonosin (PCT/US95/10284 filed Jun. 7, 1995); avirulence (avr) and disease resistance (R) genes Jones et al. (1994) *Science* 266:789; Martin et al. (1993) *Science* 262:1432; Mindrinos et al. (1994) *Cell* 78:1089; and the like.

Alterations in gene expression may also affect the type or amount of products of commercial interest; for example, starch for the production of paper, textiles and ethanol.

Another important commercial use of transformed plants is the production of polymers and bioplastics such as described in U.S. Pat. No. 5,602,321 issued Feb. 11, 1997. Genes such as B-Ketothiolase, PHBase (polyhydroxybutyrate synthase) and acetoacetyl-CoA reductase (see Schubert et al. (1988) *J. Bacteriol* 170(12):5837–5847) facilitate expression of polyhydroxyalkanoates (PHAs).

In certain embodiments the nucleic acid sequences of the present invention can be stacked with any combination of polynucleotide sequences of interest in order to create plants with a desired phenotype. For example, the various stress-responsive promoters of the present invention, including functional fragments and variants of SEQ ID NOS: 1 and 2, may be used to drive multiple genes of interest in a single plant. The combinations generated can include multiple copies of any one or more of the polynucleotides of interest. The polynucleotides of the present invention can also be stacked with any gene or combination of genes to produce plants with a variety of desired trait combinations, including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99–106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837–5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method, including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or overexpression cassettes to generate the desired combination of traits in the plant.

The nucleotide sequence operably linked to the promoter disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this way, production of the native protein encoded by the targeted gene is inhibited to achieve a desired phenotypic response. Thus the promoter sequence disclosed herein can be operably linked to antisense DNA sequences to reduce or inhibit expression of a native sequence.

The expression cassette will also include, at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Nat Acad. Sci*. USA 86:6126–6130; potyvirus leaders, for example, TEV leader (Tobacco Etch Virus), Allison et al. (1986); MDMV leader (Maize Dwarf Mosaic Virus), *Virology* 154:9–20; human immunoglobulin heavy-chain binding protein (BiP), Macejak et al. (1991) *Nature* 353:90–94; untranslated leader from the coat protein mRNA of alfalfa mosaic virus (AMV RNA 4), Jobling et al. (1987) *Nature* 325:622–625); tobacco mosaic virus leader (TMV), Gallie et al. (1989) *Molecular Biology of RNA*, pages 237–256; and maize chlorotic mottle virus leader (MCMV) Lommel et al.

(1991) *Virology* 81:382–385. See also Della-Cioppa et al. (1987) *Plant Physiology* 84:965–968. The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest under the control of the promoter. In general, the vectors should be functional in plant cells. At times, it may be preferable to have vectors that are functional in *E. coli*, facilitating, for example, the production of protein for raising antibodies, construction of inserts, DNA sequence analysis, or recovery of quantities of nucleic acids. Vectors and procedures for cloning and expression in *E. coli* are discussed in Sambrook et al. (supra).

The transformation vector, comprising the promoter sequence of the present invention operably linked to a heterologous nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the promoter. In preferred embodiments, a selectable marker and a reporter gene are also included. For ease of obtaining sufficient quantities of vector, a bacterial origin that allows replication in *E. coli* is preferred.

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *BioTechniques* 19:650–655; and Chiu et al. (1996) *Current Biology* 6:325–330.

Selectable marker genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. (1983) *EMBO J.* 2:987–992; methotrexate, Herrera Estrella et al. (1983) *Nature* 303:209–213; Meijer et al. (1991) *Plant Mol. Biol.* 16:807–820; hygromycin, Waldron et al. (1985) *Plant Mol. Biol.* 5:103–108; Zhijian et al. (1995) *Plant Science* 108:219–227; streptomycin, Jones et al. (1987) *Mol. Gen. Genet.* 210:86–91; spectinomycin, Bretagne-Sagnard et al. (1996) *Transgenic Res.* 5:131–137; bleomycin, Hille et al. (1990) *Plant Mol. Biol.* 7:171–176; sulfonamide, Guerineau et al. (1990) *Plant Mol. Biol.* 15:127–136; bromoxynil, Stalker et al. (1988) *Science* 242:419423; glyphosate, Shaw et al. (1986) *Science* 233:478–481; phosphinothricin, DeBlock et al. (1987) *EMBO J.* 6:2513–2518.

Other genes that could serve utility in the recovery of transgenic events but might not be required in the final product would include, but are not limited to, examples such as GUS (β-glucuronidase), Jefferson (1987) *Plant Mol. Biol. Rep.* 5:387); GFP (green florescence protein), Chalfie et al. (1994) *Science* 263:802; luciferase, Teeri et al. (1989) *EMBO J.* 8:343; and the maize genes encoding for anthocyanin production, Ludwig et al. (1990) *Science* 247:449.

The transformation vector comprising the particular promoter sequence of the present invention, operably linked to a heterologous nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway et al. (1986) *Biotechniques* 4:320–334; electroporation, Riggs et al. (1986) *Proc. Natl. Acad. Sci. USA* 83:5602–5606; *Agrobacterium*-mediated transformation, see for example, Townsend et al. U.S. Pat. No. 5,563,055; direct gene transfer, Paszkowski et al. (1984) *EMBO J.* 3:2717–2722; and ballistic particle acceleration, see for example, Sanford et al. U.S. Pat. No. 4,945,050; Tomes et al. (1995) in *Plant Cell, Tissue, and Organ Culture; Fundamental Methods*, ed. Gamborg and Phillips (Springer-Verlag, Berlin); and McCabe et al. (1988) *Biotechnology* 6:923–926. Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci.* USA 85:4305–4309 (maize); Klein et al. (1988) *Biotechnology* 6:559–563 (maize); Klein et al. (1988) *Plant Physiol.* 91:440–444 (maize); Fromm et al. (1990) *Biotechnology* 8;833–839; Hooydaas-Van Slogteren et al. (1984) *Nature* (London) 311:763–764; Bytebier et al. (1987) *Proc. Natl. Acad. Sci.* USA 84:5345–5349 (Liliaceae); De Wet et al. (1985) in *The Experimental Manipulation of Ovule Tissues*, ed. G. P. Chapman et al. (Longman, N.Y.), pp. 197–209 (pollen); Kaeppler et al. (1990) *Plant Cell Reports* 9:415418; and Kaeppler et al. (1992) *Theor. Appl. Genet.* 84:560–566 (whisker-mediated transformation); D. Halluin et al. (1992) *Plant Cell* 4:1495–1505 (electroporation); Li et al. (1993) *Plant Cell Reports* 12:250–255 and Christou et al. (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed can be grown into plants in accordance with conventional ways. See, for example, McCormick et al. (1986) *Plant Cell Reports* 5:81–84. These plants can then be grown, and pollinated with the same transformed strain or different strains. The resulting hybrid expressing the desired phenotypic characteristic can then be identified. Two or more generations can be grown to ensure that expression of the desired phenotypic characteristic is stably maintained and inherited.

The following examples are offered by way of illustration and not by way of limitation.

EXAMPLES

Example 1

Isolation of the Maize RIP2 Promoter

A genomic clone comprising the maize RIP2 gene was obtained as detailed (Bass et al., Plant Physiology 107: 661–662, 1995) and approximately a 1 kb region 5' to the coding region was sequenced. Maize W64A leaf genomic DNA was partially digested with Sau3A and used to produce a library of fragments in λgem11. The library was probed with a RIPcDNA clone, pZmcRIP3, and a corresponding 6.3 kb BamHI fragment was sub-cloned into the plasmid Bluescript (KS/+). Using the previous cDNA sequence data, sequencing primers were successively designed and used to establish genomic DNA sequence upstream of the ATG start codon. A subsequent engineered version was produced in order to facilitate sub-cloning of coding regions from other genes. The two versions of the promoter share identity exceeding 99% in the 990 nucleotide positions immediately 5' to the RIP2 coding sequence. PCR primers (RIP2sub-161U, GTTTTGGCCGATGCTACCCGAATTG (SEQ ID NO: 3) and RIP2sub-L, TGATGCGTCGGTACCATGGT-TATGCCAAT (SEQ ID NO: 4)) were used to amplify the promoter region from the genomic subclone, converting the region around the ATG start to a NcoI restriction site. PCR fragments were excised and cloned into the TA-cloning vector in TOP10 cells. Appropriately re-engineered subclones were identified by restriction analyses and confirmed by sequencing.

Example 2

Expression Summary for RIP2 Promoter

Various methods were used to determine the expression patterns engendered by the RIP2 promoter.

Affymetrix-style mRNA profiling: Corn plants were subjected to either water deprivation or shade stress near flowering. Samples were harvested, processed to poly-A-containing RNA, and used as labeled probes against a synthetic oligo array representing approximately 1500 corn genes. This method represents one approach to analyzing expression differences for thousands of genes between contrasting samples. When Hybrid 3732, grown in buckets, was subjected to water stress, it was found that RIP2 was significantly induced in pre-pollinated ears, pedicels, and seeds-minus-pedicels. Hybrid 3394 growing in the field was subjected to shade stress for 7 days, either immediately prior to or after pollen shed. RIP2 was found to be induced significantly in the post-pollinated ear, in both tip and butt sections.

Curagen-Based mRNA Profiling:

The polynucleotides were identified using a proprietary transcript imaging method that compares transcript patterns in two samples and allows cloning of differentially expressed fragments. This technology was developed by CuraGen (New Haven, Conn.) (see Published PCT Patent Application No. WO 97/15690, published May 1, 1997, and hereby incorporated by reference). Fluorescently-tagged, PCR amplified cDNA fragments representing expressed transcripts can be visualized as bands or peaks on a gel tracing, and the cDNA from differentially expressed (induced or suppressed) bands can be recovered from a duplicate gel, cloned, and sequenced. Known cDNAs can be identified without the need for cloning, by matching the predicted size and partially known sequence of specific bands on the tracing.

Looking at the same samples as in the 3732 X water stress experiment cited above, it was found that RIP2 was induced approximately 37-fold in the pre-pollinated ear sample and approximately 3-fold in the pedicel sample.

Microarray-based mRNA profiling: Spotting of cloned gene segments on treated glass slides offers an alternative approach to measuring gene expression; large numbers of samples can be spotted. Based upon the results cited above, RIP2 was added to a microarray and assayed in a number of different stress experiments.

Using the same shade samples cited above, RIP2 was induced in post-pollinated ear samples, up 44-fold in the butt after 5 days of shade and up 35-fold in the tip.

Repeating elements of this experiment the next year, RIP2 was induced approximately 24-fold in shaded ovaries but again was undetectable in control plants.

Using the samples from the 3732 X water stress experiments cited above, it was found that 7 days of stress induced RIP2 expression approximately 48-fold in pre-pollinated ears. Relief of that stress by watering decreased RIP2 expression below the level of detection.

In a field-based water stress experiment, it was found that RIP2 was induced 2- to 3-fold in pedicel samples after 7 and 12 days of stress. Re-watering of these plants decreased RIP2 expression to below the level of detection.

Lynx-style mRNA profiling. Lynx Therapeutics, Inc. has developed a proprietary method for isolating tens of thousands of mRNAs from tissue samples and obtaining short sequence stretches, which in many cases are sufficient for identification. Using this approach, we have identified 40–80,000 mRNAs per sample and then compared them across various corn samples and treatments. Results are expressed representationally as parts per million:

| Pedicels X drought stress: | 253 |
|---|---|
| Pedicels X control: | undetectable |

RIP2 expression was also found in two tassel samples and one root sample, but was virtually undetectable in all other samples.

The consensus result from several measures of gene expression, as described above, was that the RIP2 gene is normally undetectable in its expression in most corn tissues under "normal" growth conditions. In many tissues analyzed, imposition of stresses related to dehydration were able to induce the expression of this gene to high levels, but relief of the stress resulted in its expression dropping back below the level of detection. As such, RIP2 represents an ideal gene promoter to use in expressing stress protectant genes.

All publications and patent applications cited in the specification are indicative of the level of skill of those in the art to which this invention pertains. All publications, patents, patent applications, and computer programs cited herein are incorporated by reference to the same extent as if specifically and individually indicated to be incorporated by reference.

Although the foregoing invention has been described in some detail by way of illustration and example for purposes of clarity of understanding, it will be obvious that certain changes and modifications can be practiced within the scope of the appended claims.

That which is claimed is:

1. An expression cassette comprising an isolated nucleic acid comprising a promoter and a heterologous polynucleotide operably linked thereto, wherein said promoter comprises the polynucleotide of SEQ ID NO: 1 or SEQ ID NO: 2.

2. A transformation vector comprising the expression cassette of claim 1.

3. A plant, or plan part, stably transformed with the expression cassette of claim 1.

4. The plant or plan part of claim 3, wherein the plant part is selected from the group consisting of: cells, protoplasts, cell tissue cultures, callus, cell clumps, embryos, pollen, ovules, seeds, flowers, kernels, ears, cobs, leaves, husks, stalks, roots, root tips, anthers, and silk.

5. The plant or plan part of claim 3, wherein said plant is a monocot.

6. The plant or plan part of claim 5, wherein said monocot is maize, barley, wheat, oat, rye, sorghum or rice.

7. The plant or plan part of claim 3, wherein said plant is a dicot.

8. The plant of claim 7, wherein said dicot is soybean, alfalfa, safflower, tobacco, sunflower, cotton, or canola.

9. A method for selectively expressing a nucleotide sequence in a plant, said method comprising transforming the plant with an expression cassette comprising a promoter operably linked to said nucleotide sequence, wherein said promoter comprises the polynucleotide of SEQ ID NO: 1 or SEQ ID NO: 2.

10. The method of claim 9, wherein said nucleotide sequence encodes a polypeptide involved in phytohormone biosynthesis.

11. The method of claim 9, wherein said nucleotide sequence encodes a polypeptide involved in cell cycle regulation.

12. The method of claim 9, wherein said nucleotide sequence encodes a polypeptide involved in fatty acid metabolism.

13. The method of claim 9, wherein said nucleotide sequence encodes a polypeptide involved in carbohydrate metabolism.

14. The method of claim 9, wherein said nucleotide sequence encodes a polypeptide involved in the induction of stress-protective pathways.

15. The method of claim 14, wherein said nucleotide sequence encodes a dehydration-responsive transcription factor.

16. The method of claim 14, wherein said nucleotide sequence encodes a cold-induced transcription factor.

* * * * *